United States Patent
Hashim

(10) Patent No.: US 12,239,624 B2
(45) Date of Patent: Mar. 4, 2025

(54) GLYCERYL TRIS (BETA-HYDROXYBUTYRATE) AND NEURONAL TRANSIENT ISCHEMIC ATTACKS

(71) Applicant: NeuroEnergy Ventures, Inc., New York, NY (US)

(72) Inventor: Sami Hashim, Dobbs Ferry, NY (US)

(73) Assignee: NeuroEnergy Ventures, Inc., New York, NY (US)

( * ) Notice: Subject to any disclaimer, the term of this patent is extended or adjusted under 35 U.S.C. 154(b) by 752 days.

(21) Appl. No.: 17/608,350

(22) PCT Filed: May 30, 2019

(86) PCT No.: PCT/US2019/034592
§ 371 (c)(1),
(2) Date: Nov. 2, 2021

(87) PCT Pub. No.: WO2020/242478
PCT Pub. Date: Dec. 3, 2020

(65) Prior Publication Data
US 2022/0288006 A1    Sep. 15, 2022

(51) Int. Cl.
*A61K 31/22* (2006.01)
*A61P 25/28* (2006.01)

(52) U.S. Cl.
CPC .............. *A61K 31/22* (2013.01); *A61P 25/28* (2018.01)

(58) Field of Classification Search
CPC ........... A61K 31/22; A61P 25/28; A61P 25/00
See application file for complete search history.

(56) References Cited

U.S. PATENT DOCUMENTS

| | | | |
|---|---|---|---|
| 6,136,862 A | 10/2000 | Hirade | |
| 6,316,038 B1 | 11/2001 | Veech | |
| 6,316,938 B1 | 11/2001 | Veech | |
| 7,807,718 B2 | 10/2010 | Hashim et al. | |
| 9,925,164 B1 * | 3/2018 | Hashim | A61K 31/225 |
| 2010/0197758 A1 * | 8/2010 | Andrews | A61K 31/404 514/419 |
| 2014/0296337 A1 | 10/2014 | Greenwood et al. | |
| 2018/0177753 A1 | 6/2018 | Hashim | |
| 2018/0193300 A1 | 7/2018 | Hashim | |
| 2018/0200220 A1 * | 7/2018 | Firger | A61P 25/06 |

FOREIGN PATENT DOCUMENTS

WO    1998041201 A    9/1998

OTHER PUBLICATIONS

Campellone, J. V. and Dugdale, D. C. "Neurologic deficit". Mount Sinai, Jan. 23, 2023. (Year: 2023).*
Suzuki, et al; Jpn J. Pharmacol. 89, 36-43 (2002); Beta-Hydroxybutyrate, a Cerebral Function Improving Agent, Protects Rat Brain Against Ischemic Damage Caused by Permaqnent and Transient Focal Cerebral Ischemia.
Lundy et al; Stroke, vol. 18, No. 1, Jan.-Feb. 1987; 217-222; Elevated Blood Ketone and Glucagon Levels Cannot Account foe 1,3-butanediol Induced Cerebral Protection in the Levine Rat.
Lee et al; Exogenous Beta-Hydroxybutyrate Treatment and Neuroprotection in a Suckling Rat Model of Hypoxic-Ischemic Encephalopathy; Developmental Neuroscience 2018;40:73-83.
Smith et al; KTX 0101: A Potential Metabolic Approach t Cytoprotection in Major Surgery and Neurological Disorders; CNS Drug Reviews, vol. 11, No. 2, pp. 113-140, 2005.
Yin, Junxiang et al; 2015 J Cerebral Blood Flow & Metabolism (2015) 35, 1783-1789; Sirtuin 3 mediates neuroprotection of ketones against ischemic stroke.
Kim et al; Journal of Neurochemistry, vol. 101, No. 5, 2007, 37 pages; https:// doi.org/ 10.1111/j.1471-4159.2007.04483.x; Ketone bodies are protective against oxidative stree in neocortal neurons (Previously submitted).
Sullivan; Annals of Neurology, vol. 55, No. 4, Mar. 2004, Abstract ; https://doi.org/10.1002/ana.20062; The ketogenic diet increases mitochondrial uncoupling protein levels and activity (Previously submitted).
Guo, et al; Front Mol Neurosci Mar. 20, 2018; 11:86 6. Abstract; doi: 10.3389/fnmol.2018.00086.eCollection 2018; Ketogenic Diet Improves Brain Ischemic Tolerance and Inhibits NLRP3 Inflammasome Activation by Preventing Drpl-Mediated Mitochondrial Fission and Endoplasmic Reticulum Stress. (Previously submitted).
Shaafi, et al; Adv Pharm Bull Dec. 2014; 4(Suppl 2): 479-481; Ketogenic Diet Provides Neuroprotective Effects against Ischemic Stroke Neuronal Damages Published online Dec. 31, 2014. doi: i0.5681/apb 2014 071 (Previously submitted).
Effects of a Ketogenic Diet on Acute Stroke; https://clinicaltrials. gov/ct2/show/NCTO1997749 (6 pages) (Previously submitted).
Woodfield; Ketogenic diet could reduce brain inflammation after stroke or injury (2pages); https://www.diabetes.eo.uk/news/2017/sep/keto genic-diet-could-reduce-brain-inflammatio . . . (Previously submitted).
Stein:Health: 2018; As the keto diet gains popularity, scientists explain what we do and don't know (4pages) https://medicalxpress. com/news/2018-08-keto-diet-gains-popularity-scientists.html (Previously submitted).
Gibson, et al: J Neurochem Nov. 2012, 123(02):52-57; doi: 10 1111/i.1471-4159 2012 07943 X; Stroke outcome in the ketogenic state—a systematic review of the animal data (12 pages) (Previously submitted).
Hewings-Martin; Medical News Today; Jan. 2018 (3 pages) https:// www.medicalnewstoday.com/articles/320729.php; This diet may slow cognitive decline after stroke (Previously submitted).

(Continued)

*Primary Examiner* — Clinton A Brooks
*Assistant Examiner* — Kendall Nicole Heitmeier
(74) *Attorney, Agent, or Firm* — Irving M. Fishman

(57) ABSTRACT

A method of use of Glyceryl Tris (Beta-hydroxybutyrate) in the minimization, reduction, or prevention of neuronal deficit and/or neuronal cell death with respect to follow-on neuronal transient ischemic attacks (NTIAs) in subjects who have had (or in subjects exhibiting symptomology of having had) at least one prior NTIA.

7 Claims, No Drawings

(56) References Cited

OTHER PUBLICATIONS

Healing from a Stroke with the Ketogenic Diet—My Story; http://healing-fast-with-keto.com/home-keto-diet/heal-fast-from-the-stroke.html 2018 (6 pages) (Previously submitted).
Keto Diet May Hold key to Treatments for Brain Inflammation; Healthline; https://www.healthline.com/health-news/keto-diet-key-to-brain-inflammation-treatments (7 pages) (Previously submitted).
Suzuki et al; Jpn J Pharmacol 87 141-150 (2001); Effect of –Hydroxybutyrate, a Cerebral Function Improving Agent, on Cerebral Hypoxia, Anoxia and Ischemia in Mice and Rats (Previously submitted).
Izumi, et ali: J Clin Invst 1998; 101(5):1121-1132. https://doi.org/10.1172/JCI1009; beta-Hydroxybutyrate fuels synaptic function during development. Histologicql and physiological evidence in rat hippocampal slices. (Previously submitted).
Hashim, J. Lipid Res 55: 1818-1826; Ketone body therapy: from the ketogenic diet to the oral administration of ketone ester.
Gibson, et al: J Neurochem Nov. 2012, 123(02):52-57; doi: 10 1111/i.1471-4159 2012 07943 X; Stroke outcome in the ketogenic state—a systematic review of the animal data (12 pages).
Hewings-Martin; Medical News Today; Jan. 2018 (3 pages) https://www.medicalnewstoday.com/articles/320729.php; This diet may slow cognitive decline after stroke.
Healing from a Stroke with the Ketogenic Diet—My Story; http://healing-fast-with-keto.com/home-keto-diet/heal-fast-from-the-stroke.html 2018 (6 pages).
Keto Diet May Hold key to Treatments for Brain Inflammation; Healthline; https://www.healthline.com/health-news/keto-diet-key-to-brain-inflammation-treatments (7 pages).
Suzuki et al; Jpn J Pharmacol 87 141-150 (2001); Effect of –Hydroxybutyrate, a Cerebral Function Improving Agent, on Cerebral Hypoxia, Anoxia and Ischemia in Mice and Rats.
Izumi, et ali: J Clin Invst 1998; 101(5):1121-1132. https://doi.org/10.1172/JCI1009; beta-Hydroxybutyrate fuels synaptic function during development. Histologicql and physiological evidence in rat hippocampal slices.
Clinic Medication Compendium, Sep. 30, 2017, Edited by Changshan He et al, China Medical Science Press, p. 543 (101. Cerebral apoplexy, transient ischemic attack and cerebral embolism).
BRPTO_office_action_BR11_2021_022763_6_English_Translation.pdf.
Canadian_CA3136552_counterpart_Office_Action_2023-08-09.pdf.
CN_corresponding_CN2019800956092_Office_Action_and_Search_Report-translation-2024_02_07.pdf.
EP19930919_6_counterpart_2022-10-12-Search_Report.pdf.
IL_corresponding_288343_Office_Action_29JAN23.pdf.
JP_corresponding_application_JP2021-568387_OA_April_2023.pdf.
MY_corresponding_case_MY_PI2023005583_Substantive_Examination-2023-07-04.pdf.
Office Action of Nov. 2023 in corresponding BR Application BR11-2021-022736 6 (3pg).
Office Action of Aug. 2023 in corresponding application CA3136552 (5pg).
Office Action of Oct. 2022 in corresponding EP19930919.6 (5pgs).
Office Action of Jan. 2023 in corresponding IL 288343 (5pg).
Office Action of Apr. 2023 in corresponding JP 2021-568387 (2pg).
Office Action of Jul. 2023 in corresponding MY PI2023005583 (3pg).
Kim et al; Journal of Neurochemistry, vol. 101, No. 5, 2007, 37 pages; https:// doi.org/ 10.1111/j.1471-4159.2007.04483.x; Ketone bodies are protective against oxidative stree in neocortal neurons.
Sullivan; Annals of Neurology, vol. 55, No. 4, Mar. 2004, Abstract ; https://doi.org/10.1002/ana.20062; The ketogenic diet increases mitochondrial uncoupling protein levels and activity.
Guo, et al; Front Mol Neurosci Mar. 20, 2018; 11:86 6. Abstract; doi: 10.3389/fnmol.2018.00086.eCollection 2018; Ketogenic Diet Improves Brain Ischemic Tolerance and Inhibits NLRP3 Inflammasome Activation by Preventing Drpl-Mediated Mitochondrial Fission and Endoplasmic Reticulum Stress$_x$.
Shaafi, et al; Adv Pharm Bull Dec. 2014; 4(Suppl 2): 479-481; Ketogenic Diet Provides Neuroprotective Effects against schemic Stroke Neuronal Damages Published online Dec. 31, 2014. doi: 10.5681/apb 2014 071.
Effects of a Ketogenic Diet on Acute Stroke; https://clinicaltrials.gov/ct2/show/NCTO1997749 (6 pages).
Woodfield; Ketogenic diet could reduce brain inflammation after stroke or injury (2pages); https://www.diabetes.eo.uk/news/2017/sep/keto genic-diet-could-reduce-brain-inflammatio . . . .
Stein:Health: 2018; As the keto diet gains popularity, scientists explain what we do and don't know (4pages) https://medicalxpress.com/news/2018-08-keto-diet-gains-popularity-scientists.html.

* cited by examiner

GLYCERYL TRIS (BETA-HYDROXYBUTYRATE) AND NEURONAL TRANSIENT ISCHEMIC ATTACKS

CROSS-REFERENCE TO RELATED APPLICATIONS

Not Applicable.

STATEMENT REGARDING FEDERALLY SPONSORED RESEARCH OR DEVELOPMENT

Not Applicable

FIELD OF THE INVENTION

The present invention is directed to the field of medical foods, nutritional supplements, and medicinal agents. The present invention is also directed to uses of Glyceryl Tris (Beta-HydroxyButyrate), also known as Glyceryl Tris Butyrin, but hereinafter referred to as GTβHB. The present invention is also directed to the field of modalities in the aid of dealing with the sequellae of Neuronal Transient Ischemic Attacks (hereinafter NTIA), nutritional supplements, medical foods and medications for dealing with the sequellae of NTIA prophylactically, or any of the foregoing in the dietary management of NTIA. The invention further relates to modalities for aiding in the reduction or elimination of neurological deficits associated with NTIA and or reducing or eliminating cell death due to NTIA, particularly in the prophylactic enteral administration of GTβHB prior to a further NTIA. The present invention relates to all of the above in a subject population that is known to have had or has symptomology of one who has had a prior NTIA and is directed to offsetting or avoiding or minimizing or reducing the effects of a subsequent NTIA is such subjects.

BACKGROUND OF THE INVENTION

NTIAs in the brain are a significant health issue, especially in the older population, sand most especially in those having other conditions that affect neurologic function. Frequently, the affected person is not even aware that a NTIA has occurred and is only made aware of the fact by another who observes one or more neurologic deficit symptoms in that person. Additionally, it has been observed that once one has an initial NTIA that person is likely to have others, especially within the following few months, more particularly within a month or two, with a high proportion of such subsequent NTIAs taking place within the next 2-3 days after a prior one. Repeated NTIAs are also known to be markers for more severe strokes. NTIAs are related to more severe ischemic strokes in that NTIAs are defined as generally being less than about 1 hour in duration and the affected area is then re-perfused, typically by spontaneous dissolution of the blockage causing the ischemia or by relaxation of the arteries that are restricting blood flow (restriction typically due to arterial spasm and/or constriction which may be caused by sonic other idiopathic process or brought on by some environmental factor to which the subject is exposed or induced by some medication/nutritional supplement and/or food the subject is taking or psychological stress) or combinations thereof. Therefore, there is a need for a medical food in nutritional/dietary supplementation or treatment regimen that cart aid in the moderation or prevention of a follow-on NTIA in a subject who is known to have had or a subject who exhibits the symptomology of one who has had a prior NTIA.

Similar to strokes, NTIAs have a "core" area that is directly affected by the ischemic event, and a penumbra area that is secondarily affected. The severity of the effect in each area is dependent in part on the how long the ischemic event lasts, whether there is adequate secondary perfusion to the affected areas, and whether the particular cells in question have been subject to multiple ischemic events and how recently. Separate and distinct NTIAs significantly separated in time may not result in cumulative effects, particularly if the affected cells have been able to heal, but multiple NTIAs in relatively short periods of time (days-weeks-months) may, and often do, result in cumulative effects. Thus, there is a need for a method of helping to prevent the accumulation of neurologic deficits and other ischemic effects on brain cells.

OBJECTS OF THE INVENTION

An object of the some embodiments of the invention is to provide a method of reducing or preventing the neurologic deficit effects of a repeated neuronal transient ischemic attack (NTIA) in a subject who is known to have had or a subject who exhibits the symptomology of one who has had a prior NTIA via enteral administration of Glyceryl Tris (Betahydroxybutyrate) (hereinafter "GTβHB") in anticipation of another NTIA event taking place.

It is another object of some embodiments of the invention to provide a method of reducing or preventing ischemic event neuronal cell death due to a repeated NTIA in a subject known to have had or a subject who exhibits the symptomology of one who has had a prior NTIA via enteral administration to said subject of GTβHB in anticipation of another NTIA event taking place It is a further object of some embodiments of the invention to provide a method of preventing or reducing ischemic neuronal cell death in the core ischemic area of a subsequent NTIA in a subject known to have had or a subject who exhibits the symptomology of one who has had a prior NTIA by enteral administration of GTβHB in anticipation of another NTIA event taking place.

Even further objects of embodiments of the invention will become apparent to those of ordinary skill in the art after having benefit of the instant specification.

BRIEF SUMMARY OF THE INVENTION

In brief, the foregoing objects of the invention and others can be obtained by administration of GTβHB to a subject population either known to have bad a prior net NTIA or a subject exhibiting symptomology of one who has had a prior NTIA (and therefore suspected of having had a prior NTIA) in an of to reduce or eliminate or prevent the neuronal ischemic effects of a follow-on NTIA. Since follow-on NTIAs generally occur within days to weeks to two-three months to as much as a year after a prior NTIA, the oral administration of GTβHB is generally continued for up to 12 months (the Gross GTβHB administration Period) after a prior NTIA event. Since the typical oral administration of GTβHB is cleared by the body within a 24-hour period, oral administration of GTβHB is generally done on a daily basis in serving sizes where the daily amount is divided into fractional amounts (serving size) and administered multiple times during a 24 hour period (so that the serving size times the number of administrations is equal to the daily amount)), generally in 2-4, preferably 2-3 servings, Notwithstanding the foregoing, more frequent, smaller serving sizes can be used where desired, but because of their inconvenience of use on a more frequent schedule, more than 4 administrations per 24 hours is generally not used. Should another NTIA event occur during the Gross GTβHB Administration Period, the administration period clock is reset to start upon the recognition of the follow-on NTIA. Amounts of GTβHB orally taken on a daily basis Should be that amount which results in a blood plasma combined beta-hydroxybutyrate moiety and blood plasma acetoacetate moiety concentration of about 2 mM to 7 mM, By maintaining the level of beta-hydroxybutyrate moiety and acetoacetate moiety delivered by the GTβHB in these ranges, the neuronal deficits, cell death, etc. normally associated a subsequent NTIA taking place while the combined beta-hydroxybutyrate moiety and acetoacetate moiety blood plasma level is so maintained are reduced, eliminated or prevented.

BRIEF DESCRIPTION OF THE DRAWING

Not Applicable

DETAILED DESCRIPTION OF THE INVENTION

The present invention is directed to subjects that are known to have had or are suspected (by virtue of exhibiting symptomology of those having had a prior NTIA) of having had a prior NTIA within the preceding year, more especially to those having had or suspected of having had a prior NTIA within the prior three months, prior two months, prior one month, prior three weeks, prior 2 weeks, prior week, most especially to those having had or suspected of having had a prior NTIA within the prior 2-3 days. Upon the recognition of such prior NTIA having occurred or likely occurred. GTβHB is administered orally on a daily basis, preferably continuously (although substantially continuously with intermittent breaks in administration also being possible) for periods selected from ranges having a minimum period and maximum period selected from 2 days, 3, days, 4 days, 5 days, 6 days, 7 days, 8 days, 9 days, 10 days, 11 days, 12 days 13 days, 14 days, 15 days, 16 days, 17 days 18 days, 19 days, 20 days, 21 days, 22 days, 23 days, 24 days, 25 days, 26 days, 27 days 28 days, 29 days, 30 days, 31 days, 35 days, 42 days, 49 days, 56 days, 58 days, 59 days, 60 days, 61 days, 62 days, 63 days, 70 days, 77 days, 84 days, 90 days, 91 days, 92 days, 98 days, 105 days, 112 days, 119 days, 120 days, 126 days, 133 days, 140 days, 5 months, 6 months, 7 months, 8 months, 9 months, and 1 year, provided that the maximum is larger than the minimum. Disruption in the continuity of daily administration can be accommodated and still be within the instant invention if during the disruption portion(s) of time the subject does not suffer a further NTIA. While prompt re-administration of GTβHB after a further NTIA occurs in the discontinuation period may still be beneficial, the lack of continuity in administration results in a lack of the presence of the combined beta-hydroxybutyrate moiety and acetoacetate moiety at the time when such a discontinuation period NTIA occurred, and, therefore, the prime benefits of the present invention with respect to such discontinuation period NTIA are missed. Nonetheless, when such a discontinuation period NTIA happens, the clock for administration of the GTβHB begins anew. Furthermore while it is most beneficial to start the GTβHB regimen immediately after a first NTIA has occurred, delay in starting GTβHB administration is also possible, and is treated as if the delay is a "discontinuation period" described above. Thus, if a NTIA occurs at day zero and GTβHB administration doesn't start until day 3 but no subsequent NTIA has occurred on days 1-3, the administration period continues to count with the next day being day 4. If, however, a NTIA also occurred on day 2 (a second NTIA), then the benefits of the instant invention for such day 2 NTIA have been lost, but the day count is reset to begin with the day 2 NTIA as day zero with the purpose now being in the dietary management of a still further NTIA (or third NTIA), Without being bound by theory, the premise for the invention is that the administration of GTβHB results in perfusion of the neuronal cells in the combined beta-hydroxybutyrate moiety and acetoacetate moiety resulting in a very energy source rich environment that can be utilized when glucose is in short supply. In the healthy neuronal cells, glucose is preferentially used for energy when both glucose and ketone bodies are present. When a NTIA occurs, perfusion drops so that the neuronal cells only hate the energy sources at concentrations already present. The neuronal cells use up the available glucose first (as a preferred energy source) and after a short time, that glucose is substantially used up. Where the affected cells have the alternative energy ketone bodies present, the cells can continue to survive until those ketone bodies are depleted as well. Where the ketone bodies are present, their presence gives the cells a chance to survive for a longer period than when the ketone bodies are not present. Since NTIAs are only temporary in nature, the extra survival time afforded the affected cells may be sufficient to avoid cell death long enough for re-perfusion to take place and the affected cells rehabilitated. Because, the half-life of beta-hydroxybutyrate and acetoacetate from GTβHB is relatively short (returning to pre-administration levels within about 24 hours after a single enteral administration), administration of GTBHB is given in fractional daily amounts (servings), 2-4 times a day, preferably 3-4 times a day, and most preferably times a day GTβHB is a triester of glycerin and each of the hydroxy groups of the glycerin are esterified by a beta-hydroxybutyrate moiety. Each beta-hydroxybutyrate moiety group in each molecule is independently in either D or L form and the bulk compound being administered can be a mix of any or all of the same (i.e. a mix of compounds having (a) all of the groups in the groups in the D form, (b) all of the groups in the L form, (c) some in the D-form and some in the L-form, d) as well as mixtures of compounds selected from (1) a and b, (2) a and c, and (3) a, b, and c). Both the D and L forms of the 3-hydroxybutyroyl groups are active, however, the form is utilized more slowly and thus, it is preferable that the 3-hydroxybutyroyl groups are substantially all or all in the D form. In a particularly preferred embodiment, about 90% to 98%, more preferably about 96% of the 3-hydroxybutyroyl groups are in the D form. Nonetheless, utilization of other amounts of D vs L forms are within the invention and can be selected from 100% D to 100% L and any mixture of D and L forms in any proportions. A highly preferred embodiment is one in which the form of the compound glyceryl tris (3-hydroxybutyrate) utilized for the present invention is glyceryl tris (DL 3-hydroxybutyrate), the DL referring to the bulk compound and not necessarily a mixture in a specific molecule. These compounds and a method of manufacture thereof are described more fully in U.S. Pat. No. 7,807,718, which is incorporated herein concerning the description of the compounds and their manufacture; the relevant portions of which are re-recited herein at paragraphs 0019-0025, just prior to the instant Examples.

GTβHB is generally orally/enterally administered in an amount that is typically in the range of 0.5 g/kg per day to 2.6 g/kg body weight per day (more specifically 0.5 g/kg, 0.55 g/kg, 0.6 g/kg, 0.65 g/kg, 0.7 g/kg, 0.75 g/kg, 0.8 g/kg, 0.85 g/kg. 0.9 g/kg, 0.95 g/kg, 1 g/kg, 1.1 g/kg, 1.2 g/kg, 1.3 g/kg, 1.4 g/kg, 1.5 g/kg, 1.6 g/kg, 1.7 g/kg, 1.8 g/kg, 1.9 g/kg, 2.0 g/kg, 2.1 g/kg, 2.3 g/kg, 2.4 g/kg, 2.5 g/kg, or 2.6 g/kg, as well as amounts intermediary between any of these specifically recited amounts) in 2-3 divided doses, which for a 60 kg female is about 10-52 g/serving (more specifically 10 g/serving, 12.5 g/serving, 15 g/serving, 17.5 g/serving, 20 g/serving, 22.5 g/serving, 25 g/serving, 30 g/serving, 35 g/serving, 40 g/serving 45 g/serving, 50 g/serving, or 52 g/serving as well as amounts intermediary between any of these specifically recited amounts) thrice daily (approximately every 8 hours) to about 15-72 g/serving (more specifically 15 g/serving, 17.5 g/serving, 20 g/serving, 22.5 g/serving, 25 g/serving, 27.5 g/serving, 30 g/serving, 35 g/serving, 40 g/serving, 45 g/serving, 50 g/serving, 55 g/serving, 60 g/serving, 65 g/serving, 70 g/serving, 75 g/serving or 78 g/serving as well as amounts intermediary between any of these specifically recited amounts) twice daily (approximately every 12 hours) acid for a 70 kg male is about 12-60.7 g/serving (more specifically 12 g/serving, 15 g/serving, 17.5 g/serving, 20 g/serving, 22.5 g/serving, 25 g/serving, 30 g/serving, 35 g/serving, 40 g/serving, 45 g/serving, 50 g/serving, 55 g/serving, 60 g/serving, 55 g/serving, 60 g/serving or 60.7 g/serving as well as amounts intermediary between any of these specifically recited amounts) thrice (approximately every 8 hours) daily to about 17.5-91 g/serving (more specifically 17.5 g/serving, 20 g/serving, 22.5 g/serving, 25 g/serving, 27.5 g/serving, 30 g/serving, 35 g/serving, 40 g/serving, 45 g/serving, 50 g/serving, 55 g/serving, 60 g/serving, 65 g/serving, 70 g/serving, 75 g/serving, 80 g/serving, 85 g/serving, 90 g/serving, or 91 g/serving as well as amounts intermediary between any of these specifically recited amounts) twice (approximately every 12 hours) daily. These doses and serving sizes are intended to result in total ketone body (combined β-hydroxybutyrate and acetoacetate) blood plasma levels of 2-10 mM (more specifically 2 mM, 2.25 mM, 2.5 mM, 2.75 mM, 3 mM, 3.25 mM, 3.5 mM, 4 mM, 4.25 mM, 4.5 mM, 4.6 mM, 4.7 mM, 4.8 mM, 4.9 mM, 5.0 mM, 5.1 mM, 5.2 mM, 5.3 mM, 5.4 mM, 5.5 mM, 5.6 mM, 5.7 mM, 5.8 mM, 5.9 mM, 6.0 mM, 6.1 mM, 6.2 mM, 6.3 mM, 6.4 mM, 6.5 mM, 6.6 mM, 6.7 mM, 6.8 mM, 6.9 mM, 7.0 mM, as well as intermediary levels between any of these specifically recited levels and any of these ma serve as a lower end of a range or upper end of a range provided the upper end of the range is larger than the lower end of that range) in an average typical subject to whom these compounds are administered. (Acetoacetate is an oxidized form of β-hydroxybutyrate in which the β-hydroxy group is replaced by a β-oxo group

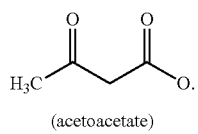

(acetoacetate)

When the GTβHB used in the present invention is ingested orally, the esters are primarily hydrolyzed in the intestinal tract due to pancreatic lipase, releasing the β-hydroxybutyrate moiety which is absorbed, and the body utilizes the β-hydroxybutyrate by converting it to acetoacetate (which, in turn, is actually used by the cells.) Those of ordinary skill in the art will know how to adjust these serving size amounts in subjects presenting with non-typical distribution and/or metabolisms such that the foregoing serving sizes do not result in the blood level being in the correct range. (Such modified amounts that are administered are considered within the scope of the invention if they raise the combined blood plasma level of β-hydroxybutyrate and acetoacetate into the range of 2 mM to 7 mM range, notwithstanding they are outside of the "serving size" ranges or bulk g of compound administered set forth elsewhere in this specification.)

The GTβHB can be administered in any enterally administrable suitable formulation, but a solution or suspension in an enterally administrable suitable carrier is preferred. Due to the relatively large serving sizes involved, traditional capsules or tablets are not generally practicable, but if one so desires to use those delivery forms, there is no reason not to use them.

In the present specification, in any case where a range of values for a particular parameter is given and a more specific recitation of values within such range is given each specific value can be the basis for a new range limit as long as the lower limit is in fact less than the upper limit. By way of example, in the foregoing paragraph, the dosage range is given as "0.5 g/kg to 2.6 g/kg" with a more specific recitation of "0.5 g/kg, 0.55 g/kg, 0.6 g/kg, 0.65 g/kg, 0.7 g/kg, 0.75 g/kg, 0.8 g/kg, 0.85 g/kg, 0.9 g/kg, 0.95 g/kg, 1 g/kg, 1.1 g/kg, 1.2 g/kg, 1.3 g/kg, 1.4 g/kg, 1.5 g/kg, 1.6 g/kg, 1.7 g/kg, 1.8 g/kg, 1.9 g/kg, 2.0 g/kg, 2.1 g/kg, 2.2 g/kg, 2.3 g/kg, 2.3 g/kg, 2.4 g/kg, 2.5 g/kg, or 2.6 g/kg". Based thereon, any of the more specific recited amounts may be the lower limit of a new range and any larger specific recited amount may be the upper limit of that new range and each such constructed range shall be deemed as specifically recited in this specification. As such, by way of example and not limitation, the ranges of 0.5 to 0.6; 0.55 to 1.9, 0.75 to 1.7, 1.8 to 1.9, etc. are all deemed recited herein. The same is applicable to the other parameters relating to dosages based on body weight, serving sizes, etc. as well.

In all references to the term "comprising" it is intended that the terms "consisting essentially of" and "consisting of" are equally disclosed. All references to any Patent or Patent Application in this specification shall be construed to including such Patent and such Patent Application as an incorporated by reference in their entirety but only to the extent that they supplement but do not contradict the specific statements in this specification. Any statement in any incorporation by reference herein, that contradicts any portion of this specification, shall be deemed null and void as an incorporation by reference of that contradictory statement. Any use of the term "about" shall be construed to mean that the last digit in the immediately following number as in the following non-limiting examples (a) "about 0.54" shall be deemed to cover the range of at least 0.535 to <0.545 and (b) "about 24" shall be construed to mean a range of at least 23.5 to <24.5. For any number preceded by "about, the absolute number shall be deemed to be disclosed as well as in "about 0.54" shall be deemed to be a specific disclosure of "0.54" as well as the range in the prior sentence.

Description of the compounds and some processes of their manufacture substantially as set forth in U.S. Pat. No. 7,807,718, which are exemplary, but not limiting disclosures, are set forth in the following 6 paragraphs.

The esters of the presently described technology can be provided in the form of dietary supplements and/or nutritional compositions. It should be understood by those skilled in the art that such dietary supplements or nutritional compositions of the present technology can be formulated utilizing conventional means. The dietary supplements or nutritional compositions can be made to any form suitable for administration to human bodies or animals. For example, oral administration of the glyceride esters of the present technology can be in the form of, without limitation, capsules, pills, liquids, tablets, edible bars, drinks, gels, thin films, gums, etc. although liquids such as solutions or suspensions are preferred.

The glyceride ester of the present technology can be produced by any available technology. For example, in one non-limiting method, it can be produced by esterification, transesterification, or interesterification of (a) glycerol and/or glyceryl ester with (b) β-hydroxybutyric acid. The esterification, transesteriftcation, or interesterification can be performed using either chemical or enzymatic catalysis.

Suitable chemical catalysts in the above esterification reactions (esterifications/interesterification/transesterifications) include, for example, without limitation, hydroxides, carbonates, bicarbonates, and alkoxide salts of alkali, alkaline earth and transition metals. Examples of alkali or alkaline earth metals include, but are not limited to, sodium, lithium, potassium, magnesium calcium, barium, iron, zinc and copper. When a chemical catalyst is used, the reaction is preferably carried out at a temperature of from about 90° C. to about 200° C., alternatively from about 120° C. to about 190° C., alternatively from about 140° C. to about 180° C.

Suitable exemplary enzymatic catalysts in the above esterification reactions (esterifications/interesterification/transesterifications) include, for example, without limitation, Candida antarctica, Candida rugosa, Aspergillus oryzae, Rhizomucor miehei, Thermomyces lanuginosa, *Pseudomonas cepacia, Pseudomonas fluorescens*, Rhizopus delemar and *Pseudomonas* sp lipases. When enzymatic catalysis is used, the reaction can be carried out at a temperature of from about 30° C. to about 75° C., alternatively from about 35° C. to about 55° C., with or without a solvent. The solvent can be, for example, hexane, heptane acetone, ethyl acetoacetate, ethyl β-hydroxybutyrate or the like.

To make a triglyceride of β-hydroxybutyric acid in accordance with at least one embodiment of the present technology, glycerol can be treated with tert-butyl β-hydroxybutyrate at a temperature of from about 110° C. to about 120° C., alternatively from about 60° C. to about 180° C., for approximately 14 to 21 hours, alternatively 3 to 21 hours. The reaction is preferably provided in an inert (e.g., nitrogen) atmosphere. During the reaction, tert-butyl alcohol by-product can be removed, for example, via distillation. At the end of the reaction, the remaining tert-butyl β-hydroxybutyrate can be removed through distillation (e.g., at about 59 to about 75° C., 1 mmHg). The product obtained may be deodorized, for example, by the addition of water under vacuum (e.g., 1 mmHg) at a temperature range of from about 50° C. to about 80° C. The structure can be confirmed through, for example nuclear magnetic resonance (NMR), elemental analyses (C,H,N) and/or gas chromatography (GC).

In accordance with at least one other embodiment of the present technology, glycerol can be treated with ethyl β-hydroxybutyrate in the presence of a lipase at from about 55° C. to about 70° C., alternatively from about 20 to about 75, for approximately 14 to 48 hours, alternatively 20 to 36 hours. The lipase can be, for example, without limitation, Novozyme® 435, Lipozyme® RM IM, or Lipozyme® TL IM, all available from Novozymes A/S, Franklinton, N.C. The reaction can be performed in an inert (e.g., nitrogen) atmosphere. During the reaction, ethyl alcohol by-product can be removed, for example, via distillation. At the end of the reaction, the remaining ethyl β-hydroxybutyrate can be removed through distillation (e.g., at 60° C., 1 mmHg). The structure of the glyceryl tris (β-hydroxybutyrate) produced can be confirmed through, for example, without limitation, NMR analysis, elemental analyses (C,H,N), and/or GC.

EXAMPLES

The following examples exemplify, but do not limit, the present invention.

Example 1 an Invention Embodiment

A first 60 kg female subject is found to have had (day zero) a NTIA and is begun on art oral regimen of GTβHB 40 g/administration, 3 times a day beginning on the next day (day 1). 2 days later (day 3) the subject has a further NTIA and continues with taking the GTβHB for the next 55 days.

Example 2 Comparison Example not of the Invention

A second 60 kg female subject is also found to have had (day zero) a NTIA but does not initiate any GTβHB administration. A further NTIA occurs on day 3 (2 days later). The subject does not initiate any GTβHB administration.

Example 3 an Invention Embodiment

A third 60 kg female subject is also found to have had (day zero) a NTIA but does not initiate any GTβHB administration. A further NTIA occurs on day 3 (2 days later). The subject then initiates an oral regimen of GTβHB 40 g/administration, 3 times a day beginning on the next day (day 4) and continues on this regimen for the next 54 days (through day 60).

Example 4 an Invention Embodiment

A fourth 60 kg female subject is found to have had (day zero) a NTIA and is begun on an oral regimen of GTβHB 40 g/administration, 3 times a day beginning on the next day (day 1). 2 days later (day 3) the subject has a further NTIA and continues with taking the GTβHB for the next 28 days. The subject then stops taking the GTβHB on day 29, and restarts taking GTβHB on day 35, and stops taking GTβHB on day 60.

Example 5 an Invention Embodiment

A fifth 60 kg female subject is found to have had (day zero) a NTIA and is begun on an oral regimen of GTβHB 40 g/administration, 3 times a day beginning on the next day (day 1). 2 days later (day 3) the subject has a further NTIA and continues with taking the GTβHB for the next 28 days. The subject then stops taking the GTβHB on day 29, a NTIA takes place on day 33 and the subject restarts taking GTβHB on day 35 from the first NTIA (and day 2 from the second TIA), and stops taking GTβHB on day 60 from the first NTIA (day 27 from the second TIA).

Example 6

Examples 1 and 3-5 are repeated except that when the subject is to receive GTβHB, the subject receives 30 g GTβHB per serving, 4 servings per day.

Example 7

Examples 1-5 are repeated except that the subject in question is a 70 kg male and when the subject is to receive GTβHB, the subject receives about 47 g per serving 3 times a day

Example 8

Example 7 is repeated except that when the subject is to receive GTβHB, the subject receives 70 g per serving twice a day.

Example 9

Examples 1 and 3-7 are repeated except that the total daily amounts that subjects receiving GTβHB, are given 1 g/kg/day rather than the 2 g/kg/day of Examples 1, and 3-7, so that the serving sizes mentioned in Examples 1, and 3-7 are cut in half for this Example.

Example 10—In Vitro Example in Support of the Invention

Rodent brain cells are bathed in nutrient medium and separated into multiple subparts. A first subset continues to receive the nutrient medium as before and serves as a control. A second subset stops replenishment of the nutrient medium and is sampled at 1 hour after halting the replenishment. A third subset has the nutrient medium slowly filtered off over a period of 30 minutes and this subset is sampled at the end of 30 minutes and again at 1 hour after the filtration began. The second and third subsets simulate a first ischemic condition analogous to that occurring in NTIA events. The second and third subsets then have the nutrient medium restored and replenished as initially provided for 2 days. Each of the second and third subgroups are further divided into 3 further subgroups each, 2a, 2b, 2c, 3a, 3b, and 3c. Each of the 2a and 3a subgroups are subjected to their respective simulated ischemic event protocol as described above. Each of subgroups 2b and 3b are subjected to their respective simulated ischemic events as described for subgroups 2a and 3a except that GTβHB is included in the nutrient medium upon restoration of the nutrient medium after the second simulated ischemic event. Subgroups 3a and 3b parallel subgroups 2a and 2b except that the GTβHB is added to the nutrient medium one day aider the first simulated ischemic event and maintained in the nutrient medium until initiating the second ischemic event. Each of the various groups are sampled to determine the relative amounts of cell death and survival. Of particular relevance is the difference between the groups 2b vs. 3b as well as 2c vs. 3c, which are comparisons between only having GTβHB after the subsequent ischemic event v. having GTβHB present in the cellular environment before and at the time of the ischemic event. These comparisons will show benefits for the pre ischemic event administration of GTβHB so as to have GTβHB present in the cellular environment when the ischemic event occurs over only administration of GTβHB only after the ischemic event in question.

The invention claimed is:

1. A method of reducing or preventing neurological deficit and/or neuronal cell death in a human subject, said subject having had a prior neuronal transient ischemic attack (NTIA) wherein said neurological deficit and/or neuronal cell death reduction or prevention is relative to that level occurring in the absence of addressing such potential deficit or death, the instant method comprising orally administering glyceryl tris (beta-hydroxybutyrate) (GTβHB) to said subject on a daily basis in a daily amount calculated to result in a combined beta-hydroxybutyrate moiety and acetoacetate blood plasma concentration of 2 mM to 7 mM in 1-4 fractional servings per day for an administration period having a range selected from the group of ranges having a minimum and a maximum independently selected from the group consisting of 2 days, 3, days, 4 days, 5 days, 6 days, 7 days, 8 days, 9 days, 10 days, 11 days, 12 days 13 days, 14 days, 15 days, 16 days, 17 days 18 days, 19 days, 20 days, 21 days, 22 days, 23 days, 24 days, 25 days, 26, days, 27 days, 28 days, 29 days, 30 days, 31 days, 35 days, 42 days, 49 days, 56 days, 58 days, 59 days, 60 days, 61 days, 62 days, 63 days, 70 days, 77 days, 84 days, 90 days, 91 days, 92 days, 98 days, 105 days, 112 days, 119 days, 120 days, 126 days, 133 days, 140 days, 5 months, 6 months, 7 months, 8 months, 9 months, and 1 year proved said minimum is less than said maximum, said administration period counting the days from said previous NTIA, where said previous NTIA date is counted as day zero, optionally interrupted by one or more days, and wherein the occurrence of a follow-on NTIA resets the day count to day zero on the day of the follow-on NTIA.

2. The method of claim 1 wherein said neuronal cell death reduction or prevention is reduction or prevention of neuronic cell ischemic core cell death until reperfusion can be re-established.

3. The method of claim 1 wherein said neuronal cell death reduction or prevention is reduction or prevention of neuronic cell ischemic penumbra cell death.

4. The method of claim 1 wherein said neurological deficit reduction or prevention is associated with neuronic ischemic core cell impairment.

5. The method of claim 1 wherein said neurological deficit reduction or prevention is associated with neuronic ischemic penumbra cell impairment.

6. The method of claim 1 wherein the daily amount of said GTβHB is administered in 2-3 divided servings per day such that the total daily amount resulting from the number of servings times the serving size is selected from 0.5 g/kg/day to 2.6 g/kg/day.

7. A method of reducing or preventing brain cell neurological deficit and/or brain cell neuronal cell death in a human subject, said subject having had a prior neuronal transient ischemic attack (NTIA) wherein said neurological deficit and/or neuronal cell death reduction or prevention is relative to that level occurring in the absence of addressing such potential deficit or death, the instant method comprising orally administering glyceryl tris (beta-hydroxybutyrate) (GTβHB) to said subject on a daily basis in a daily amount calculated to result in a combined beta-hydroxybutyrate moiety and acetoacetate blood plasma concentration of 2 mM to 7 mM in 1-4 fractional servings per day for an administration period having a range selected from the group of ranges having a minimum and a maximum independently selected from the group consisting of 2 days, 3, days, 4 days, S days, 6 days, 7 days, 8 days, 9 days, 10 days, 11 days, 12 days 13 days, 14 days, 15 days, 16 days, 17 days 18 days, 19 days, 20 days, 21 days, 22 days, 23 days, 24 days, 25 days, 26, days, 27 days, 28 days, 29 days, 30 days, 31 days, 35 days, 42 days, 49 days, 56 days, 58 days, 59 days, 60 days, 61 days, 62 days, 63 days, 70 days, 77 days, 84 days, 90 days, 91 days, 92 days, 98 days, 105 days, 112 days, 119 days, 120 days, 126 days, 133 days, 140 days, 5 months, 6 months, 7 months, 8 months, 9 months, and 1 year proved said minimum is less than said maximum, said administration period counting the days from said previous NTIA, where said previous NTIA date is counted as day zero, optionally interrupted by one or more days, and wherein the occurrence of a follow-on NTIA resets the day count to day zero on the day of the follow-on NTIA.

* * * * *